(12) United States Patent
Hu et al.

(10) Patent No.: US 10,571,403 B2
(45) Date of Patent: Feb. 25, 2020

(54) SYSTEMS AND METHODS FOR TESTING AND DIAGNOSING MALFUNCTIONS IN A LIQUID DISPENSER

(75) Inventors: Bao Zhong Hu, Shanghai (CN); Ting Deng, Shanghai (CN); Ruguo Hu, Shanghai (CN); Michael Marszalec, South Beloit, IL (US)

(73) Assignee: Societe des Produits Nestle S.A., Vevey (CH)

( * ) Notice: Subject to any disclaimer, the term of this patent is extended or adjusted under 35 U.S.C. 154(b) by 1478 days.

(21) Appl. No.: 13/994,985

(22) PCT Filed: Dec. 9, 2011

(86) PCT No.: PCT/EP2011/072271
§ 371 (c)(1),
(2), (4) Date: Jul. 26, 2013

(87) PCT Pub. No.: WO2012/080101
PCT Pub. Date: Jun. 21, 2012

(65) Prior Publication Data
US 2013/0304398 A1 Nov. 14, 2013

(30) Foreign Application Priority Data
Dec. 15, 2010 (CN) .......................... 2010 1 0594515

(51) Int. Cl.
*A47J 31/44* (2006.01)
*G06F 17/40* (2006.01)
*G06F 19/00* (2011.01)
*G01N 21/88* (2006.01)
*G06F 11/30* (2006.01)
*B67D 1/00* (2006.01)
*B67D 1/08* (2006.01)
*B67D 3/00* (2006.01)
*G16H 40/40* (2018.01)

(52) U.S. Cl.
CPC .............. *G01N 21/88* (2013.01); *A47J 31/44* (2013.01); *B67D 1/0042* (2013.01); *B67D 1/0878* (2013.01); *B67D 3/0074* (2013.01); *G06F 11/3058* (2013.01); *G06F 19/00* (2013.01); *G06F 17/40* (2013.01); *G16H 40/40* (2018.01)

(58) Field of Classification Search
None
See application file for complete search history.

(56) References Cited

U.S. PATENT DOCUMENTS 2,883,255 A * 4/1959 Anderson ................ B41J 11/36
340/518
3,813,922 A * 6/1974 Oswald ............... H01M 2/0242
73/49.2

(Continued)

*Primary Examiner* — Alexander Satanovsky
*Assistant Examiner* — Brent A. Fairbanks
(74) *Attorney, Agent, or Firm* — K&L Gates LLP

(57) ABSTRACT

Systems and methods for testing and diagnosing malfunctions in a liquid dispenser are provided. In a general embodiment, the present disclosure provides a testing and diagnosing system including a pre-tester configured to test for and collect testing data regarding an operational status of the liquid dispenser and in communication with the liquid dispenser, a communication central module configured to receive information from the testing device and the pre-tester, and a database management system configured to operate, monitor and control the testing device, the pre-tester and/or the communication central module.

32 Claims, 4 Drawing Sheets

(56) References Cited

U.S. PATENT DOCUMENTS

| | | | | |
|---|---|---|---|---|
| 5,415,329 A * | 5/1995 | Westlund | ............ | B67D 1/0832 |
| | | | | 222/397 |
| 6,542,841 B1 * | 4/2003 | Snyder | ............... | H04B 10/0795 |
| | | | | 372/26 |
| 6,735,496 B1 | 5/2004 | Roman | | |
| 7,949,901 B2 * | 5/2011 | Yano | .................... | G06F 11/263 |
| | | | | 714/33 |
| 8,112,669 B2 * | 2/2012 | Zimmerman | ....... | G06F 11/2294 |
| | | | | 714/27 |
| 8,893,133 B2 * | 11/2014 | Arnold | .................. | G06F 9/4881 |
| | | | | 718/102 |
| 8,893,138 B2 * | 11/2014 | Arnold | .................. | G06F 9/4881 |
| | | | | 718/102 |
| 2002/0101346 A1 * | 8/2002 | Busick | ................ | B67D 3/0032 |
| | | | | 340/521 |
| 2003/0041745 A1 * | 3/2003 | Laflamme | ................ | F24C 7/08 |
| | | | | 99/474 |
| 2003/0109938 A1 * | 6/2003 | Daum | ................ | H04L 12/2803 |
| | | | | 700/11 |
| 2003/0158626 A1 | 8/2003 | Goggin et al. | | |
| 2004/0231411 A1 | 11/2004 | Drube et al. | | |
| 2005/0278597 A1 | 12/2005 | Miguelanez et al. | | |
| 2007/0023536 A1 | 2/2007 | Baston | | |
| 2007/0056295 A1 * | 3/2007 | De Vilbiss | ............ | B67D 1/0869 |
| | | | | 62/3.64 |
| 2007/0233509 A1 * | 10/2007 | Buchman | ............ | G01R 31/2836 |
| | | | | 324/600 |
| 2008/0244317 A1 * | 10/2008 | Yano | ..................... | G06F 11/263 |
| | | | | 714/37 |
| 2009/0049344 A1 * | 2/2009 | Kawamura | ......... | F24D 19/1051 |
| | | | | 714/46 |
| 2010/0288791 A1 * | 11/2010 | Myyrylainen | ....... | B67D 1/0009 |
| | | | | 222/113 |
| 2011/0055632 A1 * | 3/2011 | Zimmerman | ....... | G06F 11/2294 |
| | | | | 714/31 |
| 2012/0054756 A1 * | 3/2012 | Arnold | .................. | G06F 9/4881 |
| | | | | 718/102 |
| 2012/0260255 A1 * | 10/2012 | Arnold | .................. | G06F 9/4881 |
| | | | | 718/102 |

* cited by examiner

SYSTEMS AND METHODS FOR TESTING AND DIAGNOSING MALFUNCTIONS IN A LIQUID DISPENSER

CROSS REFERENCE TO RELATED APPLICATIONS

The present application is a National Stage of International Application No. PCT/EP2011/072271, filed on Dec. 9, 2011, which claims priority to Chinese Patent Application No. 201010594515.0, filed Dec. 15, 2010, the entire contents of which are being incorporated herein by reference.

BACKGROUND

The present disclosure generally relates to methods and systems for testing and diagnosing malfunctions in an operational apparatus. More specifically, the present disclosure relates to methods and systems for testing and diagnosing malfunctions in a cooling or heating apparatus.

There are tens of millions of liquid dispensers currently in use. Many of them are returned a reconditioning or repair. In North America, many home appliance manufacturers and distributors are facing severe problem dealing with these returns. The problems generally relate to testing and diagnosing malfunctions in the liquid dispenser, which can be very time consuming and labor intensive.

SUMMARY

The present disclosure provides systems and methods for testing and diagnosing malfunctions in a heating or cooling apparatus such as a liquid dispenser. In a general embodiment, the present disclosure provides a liquid dispenser testing and diagnosing system including a liquid dispenser, a pre-tester configured to test for and collect testing data regarding an operational status of the liquid dispenser and in communication with the liquid dispenser, a communication central module configured to receive information from the testing device and the pre-tester, and a database management system configured to operate, monitor and control the testing device, the pre-tester and/or the communication central module. In an embodiment, the liquid dispenser testing and diagnosing system further includes a responding module configured to relay information between the testing device and the communication central module.

In an embodiment, the liquid dispenser testing and diagnosing system further includes a testing device configured for evaluating one or more conditions in the liquid dispenser. The testing device is in communication with the liquid dispenser. The testing device can include an electrical safety tester and/or an air leakage detector.

In an embodiment, the pre-tester is configured to determine one or more parameters of the liquid dispenser including compressor instant amps, cooling amps, heating amps, cut in/off time, heating temperature, cooling temperature or a combination thereof. In an embodiment, the pre-tester includes a pre-test box and one or more components such as a bar code scanner, a temperature sensor, a humidity sensor or a combination thereof.

In an embodiment, the pre-tester is configured to cut off a power supply to the liquid dispenser in case of a short circuit. In another embodiment, the pre-tester is configured to detect and auto-calibrate the temperature of the liquid dispenser and/or complete hardware diagnostics upon start-up of the system.

In another embodiment, the present disclosure provides a system for testing and diagnosing malfunctions in a heating or cooling apparatus. The system includes 1) a testing device for monitoring one or more conditions in an apparatus, 2) a pre-tester configured to measure an electrical current and a temperature change in the heating or cooling apparatus, 3) a communication central module configured to receive information from the testing device and the pre-tester and configured monitor environmental temperature and humidity, and 4) a database management system configured to operate, monitor and control the testing device, the pre-tester and/or the communication central module. The database management system is programmed with an algorithm to determine whether the conditions are within or outside of specifications In an embodiment of the system, the system includes a responding module configured to relay information between the testing device and the communication central module. In an embodiment of the system, the testing device includes an electrical safety tester and/or an air leakage detector. In an embodiment of the system, the database management system includes a computer display.

In an embodiment of the system, the pre-tester is configured to determine one or more parameters of the heating or cooling apparatus such as compressor instant amps, cooling amps, heating amps, cut in/off time, heating temperature, cooling temperature or a combination thereof. In an embodiment of the system, the pre-tester includes one or more components such as a bar code scanner, a temperature sensor, a humidity sensor or a combination thereof. In an embodiment of the system, the pre-tester is configured to cut off a power supply to the heating or cooling apparatus in case of a short circuit. In an embodiment of the system, the pre-tester is configured to detect and auto-calibrate the temperature of the heating or cooling apparatus and complete hardware diagnostics upon start-up of the system.

In an alternative embodiment, the present disclosure provides a method for testing and diagnosing malfunctions in a liquid dispenser during manufacturing of the liquid dispenser. The method comprises testing the manufactured liquid dispenser with at least one of an electrical safety tester or an air leakage detector. The liquid dispenser includes a water tank. The method further comprises measuring an electrical current in a circuit of the liquid dispenser and a temperature change of water in the water tank using a pre-tester configured to test for and collect testing data regarding the operational status of the liquid dispenser, and determining a pass/fail status of the liquid dispenser based on the measured electrical current and the temperature change when compared to pre-set parameters of the electrical current and the temperature change for the liquid dispenser.

In an embodiment, the method comprises cleaning the liquid dispenser if the liquid dispenser receives a pass from the pre-tester, and testing the washed liquid dispenser with at least one of an electrical safety tester or an air leakage detector. In another embodiment, the method comprises repairing the liquid dispenser if the liquid dispenser receives a fail from the pre-tester.

In an embodiment, the method comprises printing out the pass/fail status of the dispenser after the pass/fail status has been determined. In another embodiment, the method comprises scanning a bar code located on the liquid dispenser with a bar code scanner in communication with the pre-tester (e.g., via wireless bar code scanner or bar code scanner in communication with a bar code data distributor) to determine pre-set pass/fail parameters for the scanned liquid dispenser.

In an embodiment of the method, the pre-tester is in communication with a database management system including a computer display. In another embodiment of the method, the pre-tester is configured to determine one or more parameters of the liquid dispenser such as compressor instant amps, cooling amps, heating amps, cut in/off time, heating temperature, cooling temperature or a combination thereof. In yet another embodiment of the method, the electrical safety tester and the air leakage detector are in communication with a responding module that is in communication with a database management system.

In another embodiment, the present disclosure provides a method for testing and diagnosing malfunctions in a liquid dispenser. The method comprises connecting a pre-tester to a liquid dispenser including a water tank. The pre-tester is configured to receive data regarding the operational status of the liquid dispenser. The method further comprises measuring an electrical current in a circuit of the liquid dispenser and a temperature change of water in the water tank using the pre-tester, and determining a pass/fail status of the liquid dispenser based on the measured electrical current and the temperature change when compared to pre-set parameters of the electrical current and the temperature change for the liquid dispenser.

In an embodiment, the method comprises scanning a bar code located on the liquid dispenser with a bar code scanner in communication with the pre-tester to determine pre-set pass/fail parameters for the liquid dispenser. In another embodiment, the method comprises printing out the pass/fail status of the dispenser after the pass/fail status has been determined by the pre-tester. In yet another embodiment, the method comprises testing the liquid dispenser with at least one of an electrical safety tester or an air leakage detector.

In an embodiment of the method, the pre-tester is in communication with a database management system including a computer display. In another embodiment, the pre-tester is configured to determine one or more parameters of the liquid dispenser such as compressor instant amps, cooling amps, heating amps, cut in/off time, heating temperature, cooling temperature or a combination thereof.

In still another embodiment, the present disclosure provides a method for testing and diagnosing malfunctions in a heating or cooling apparatus. The method comprises testing a heating or cooling apparatus with at least one of an electrical safety tester or an air leakage detector. The heating or cooling apparatus includes a heated or cooled unit. The method further comprises measuring an electrical current in a circuit of the heating or cooling apparatus and a temperature change of the heated or cooled unit using a pre-tester configured to measure an electrical current and a temperature change in the heating or cooling apparatus, and determining a pass/fail status of the heating or cooling apparatus based on the measured electrical current and the temperature change when compared to pre-set parameters of the electrical current and the temperature change for the heating or cooling apparatus. In an embodiment, the method comprises repairing the heating or cooling apparatus if the heating or cooling apparatus receives a fail from the pre-tester.

In an embodiment, the method comprises preliminarily scanning the heating or cooling apparatus using a bar code scanner to determine the pre-set parameters of the electrical current and the temperature change for the heating or cooling apparatus. In another embodiment, the method comprises wirelessly printing a label for the heating or cooling apparatus based on the pass/fail status. In an embodiment, the method comprises calibrating a temperature probe and a current sensor of the pre-tester.

An advantage of the present disclosure is to provide an improved system for testing and diagnosing malfunctions in a liquid dispenser.

Another advantage of the present disclosure is to provide an improved system for testing and diagnosing malfunctions in a heating or cooling apparatus.

Still another advantage of the present disclosure is to provide an improved method for testing and diagnosing malfunctions in heating or cooling apparatuses on a large scale (e.g., up to 200 at a time) during manufacturing.

Yet another advantage of the present disclosure is to provide an improved point-of-use system and method for testing and diagnosing malfunctions in a heating or cooling apparatus.

Additional features and advantages are described herein, and will be apparent from, the following Detailed Description and the figures.

DETAILED DESCRIPTION

Figure 1:
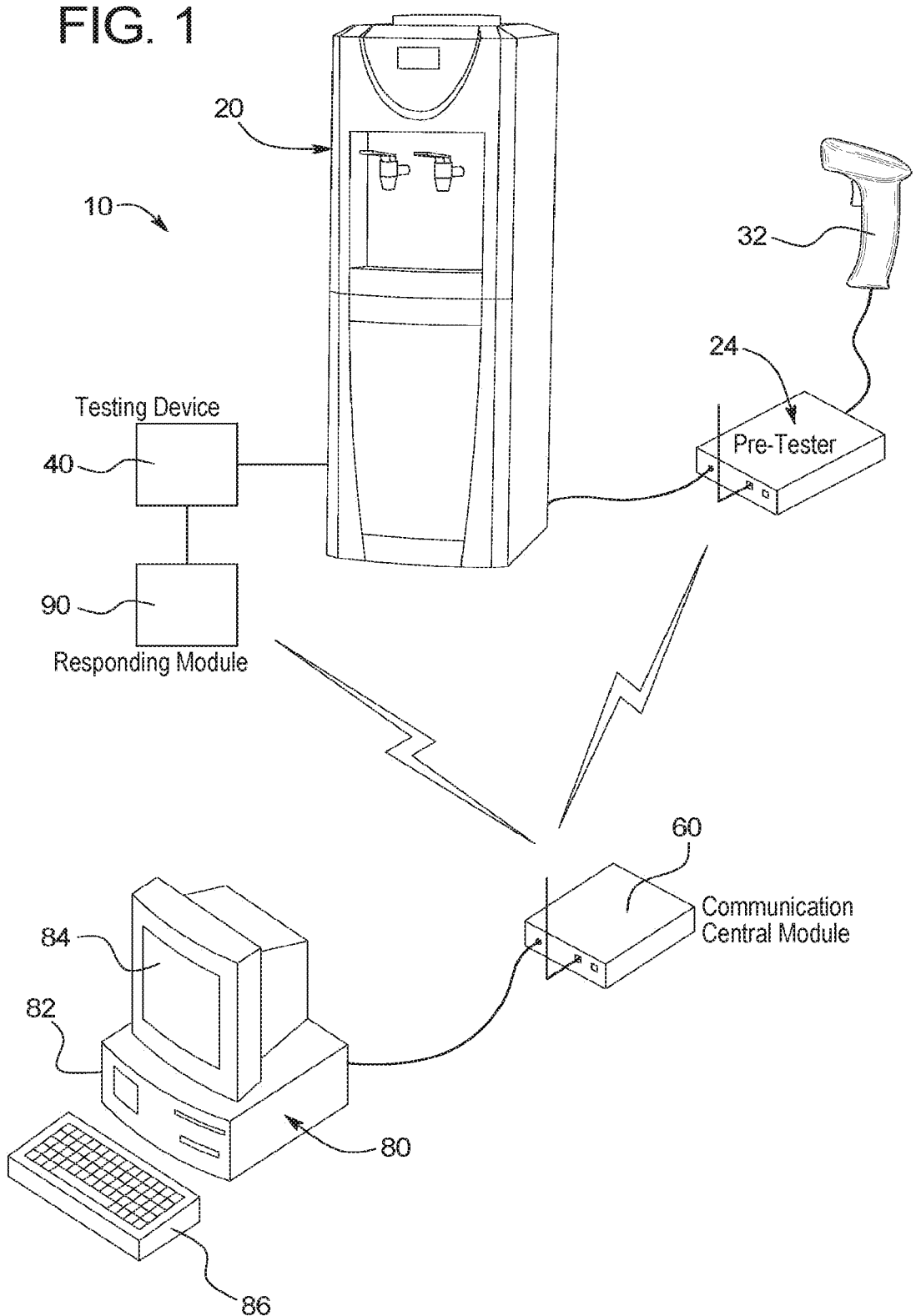
FIG. 1 shows a testing and diagnosing system in an embodiment of the present disclosure.

The present disclosure provides systems and methods for testing and diagnosing malfunctions in a heating or cooling apparatus such as a liquid dispenser. The systems and methods can be advantageously used during the large-scale manufacture of the operational apparatuses or for point-of-use locations such as at a home or business.

In a general embodiment, a core component (i.e., a pre-tester) of the testing and diagnosing systems measures the temperature/temperature change and electrical current (i.e., amperage) of the cooling/heating apparatus during start-up and running of the cooling/heating apparatus. Observable deficiencies such as the frost line in cold tank of a water cooler can be checked and recorded by an operator. In order to improve testing/diagnosing efficiency while enabling easy operation and the ability to acquire/analyze testing data, the testing and diagnosing systems can also include one or more additional features including: 1) acquisition of actual testing data for individual components of the cooling/heating apparatus, 2) automatically judge NG/GO (i.e., fault/pass) without an operator, 3) shorten heating up or cooling down time of the cooling/heating apparatus, 4) accommodate various models of the cooling/heating apparatus from different suppliers, 5) determine upper and lower limit for data/parameters for an operable cooling/heating apparatus, add electrical safety test results, and automatically populate results to a database management system, 6) add air leakage test results and integrate results to a database management system, and/or 7) print NG labels with fault description and possible reasons.

As used herein, the term compressor "instant amps" means the electrical amps needed to start up the motor, for example, of a compressor for a tested cooling/heating apparatus. The initial amount of amps needed are at the peak of power draw and then will reduce significantly to a normal/ average number. This can indirectly tell, for example, if the refrigerant inside a cooling apparatus is enough (e.g., no loss due to leakage). It should be appreciated that the same testing principle also works for thermoelectric chip cooling. The only difference is the algorithm programmed.

As used herein, the term "cooling amps" means the normal amps needed when only the compressor or thermoelectric chip is running to cool down.

As used herein, the term "heating amps" means the normal amps needed when only the heater is running to heat up.

As used herein, the term "cut in/off time" means a designated time when the water inside the water tank is heated up/cooled down. When a preset temperature is reached then the heater/cooler is cut off (cut-off time). The water inside the water tank will slowing begin cooling down/warming up due to energy transfer. When temperature of the water tank reaches a preset number, the heater/cooler is turned on again to heat up/cool down the water (cut-in time). This time difference (it is known how much water inside the tank) provides the operation efficiency of the heating/cooling system (insulation, heat transfer etc) and the wattage of the heater/cooler.

As used herein, the term "heating temperature" means the pre-determined temperature needed to be reached when the heater will be cut off.

As used herein, the term "cooling temperature" means the pre-determined temperature needed to be reached when the compressor or thermoelectric chip will be cut off.

As described herein, the "communication" of any devices can be via either wireless or wired connections.

In an general embodiment shown in FIG. 1, the present disclosure provides a testing and diagnosing system 10 for testing and diagnosing malfunctions in a liquid dispenser 20 (e.g., a heating or cooling apparatus). Testing and diagnosing system 10 includes a pre-tester 24, a communication central module 60 and a database management system 80. The liquid can be an suitable liquid such as water, coffee, soda or any other suitable beverage.

Pre-tester 24 is configured to test for and collect testing data regarding an operational status of liquid dispenser 20 and is in communication with liquid dispenser 20. Generally, pre-tester 24 is a testing/diagnosis device that tests a heating or cooling apparatus for malfunctions.

Pre-tester 24 can be configured to measure an electrical current and a temperature change in liquid dispenser 20 (e.g., various components of liquid dispenser 20) and is in direct or indirect communication with liquid dispenser 20. For example, a current sensor can be incorporated into liquid dispenser 20 and in communication with pre-tester 24. Alternatively, a current sensor can be incorporated into pre-tester 24 and connected to the electrical circuitry of liquid dispenser 20 in any suitable manner. By measuring the electrical current (e.g., detecting amperage change of cooling/heating during start-up and running) and temperature change, pre-tester 24 can use this information to tell if the testing is successful or not and also can indicate any failed parts of the heating or cooling apparatus as discussed in more detail below.

Figure 2:
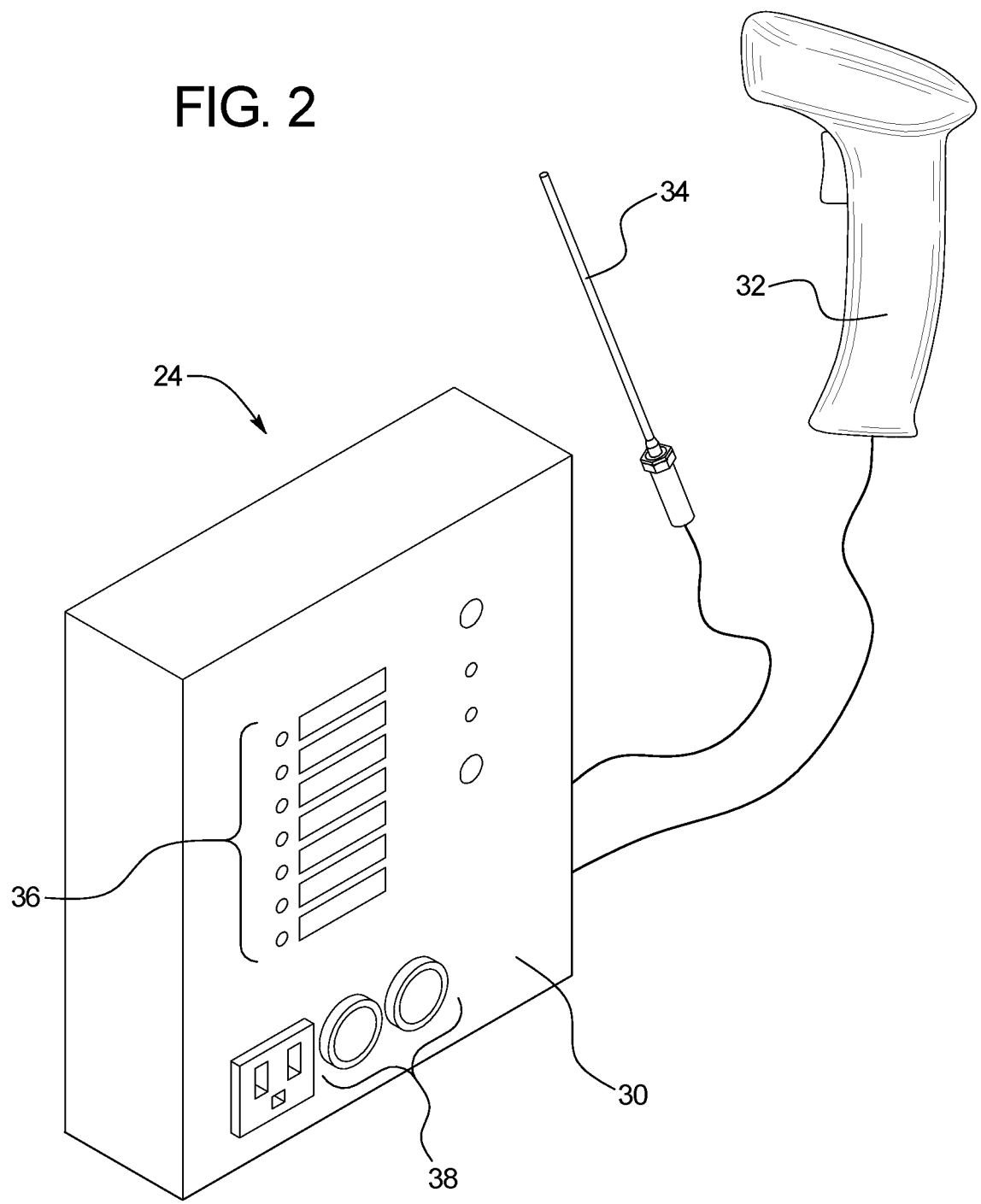
FIG. 2 shows a pre-tester in an embodiment of the present disclosure.

As further shown by FIGS. 1-2, in an embodiment, pre-tester 24 can include a pre-test box 30 and a bar code scanner 32 and a temperature probe 34 in communication with pre-test box 30. Temperature probe 34 can be inserted into the heating or cooling tank for detecting the temperature change. In another embodiment, pre-tester 24 includes an internal or external temperature sensor and humidity sensor (not shown) for monitoring environmental conditions. In another embodiment, the bar code scanner 32 can be incorporated within the pre-test box 30, which allows the pre-tester 24 to be optimized as a hand-set for ease of portability.

In an alternative embodiment, a bar code scanner and/or a temperature probe are not directly attached to a pre-tester (e.g., via a wire) but can communicate wirelessly with pre-tester. In this case, a wireless/blue-tooth bar code scanner is recommended.

In an embodiment, a pre-tester can further be in communication with a bar code data distributor that is in communication with a bar code scanner. For example, the bar code scanner can send bar code data to the bar code data distributor. The bar code data distributor can receive the bar code data acquired and sent by the bar code scanner, and then distribute this information to the pre-tester that is activated. In this way, wireless communication between the pre-test box and the bar code scanner can be realized. For example, when one bar code is acquired, the bar code data distributor can spread a wireless signal in a certain area to be acquired by a pre-test box (with a built-in receiving module inside) via a START button (e.g., shown as 38). Hence, there does not need to be any direct connection between the bar code scanner and the pre-tester.

In alternative embodiments, the bar code data distributor can either be a separate box connecting to a bar code scanner via a COM port, or be built into the bar code scanner. For example, the combination can be configured to acquire any suitable bar code data and then distribute the bar code data to the pre-tester. Alternatively or in addition to, signal communications between the bar code scanner and the responding pre-test box can be achieved by either wireless (433M)/blue-tooth, or wiring connection via a COM port.

Pre-tester 24 can also include a series of diagnostic check lights 36 (e.g., light emitting diode lights) signifying the test or diagnosing being performed. One or more status buttons 38 of any color (e.g., red, green) can initiate/terminate operation of and/or provide the status of pre-tester 24 (e.g., on, off, running, pass, fail). For example, in an embodiment, a first green status button can be labeled as START, meaning if pressed down, pre-tester 24 will start from bar code acquiring. A second red status button can be labeled for Emergency STOP, meaning if pressed down, the power supply to water dispenser will be cut of immediately for safety. In another embodiment, a first green status button can be labeled as START C/C, meaning if the water dispenser only has a cooling function, an operator should press down this button to start pre-tester 24 online. A second red status button labeled as START H/C can be used only for a water dispenser with both heating and cooling functions.

In an embodiment, the features and functions of pre-tester 24 can include one or more of: 1) acquiring bar code information, 2) cutting off power supply to liquid dispenser 20 in case of short/shut circuit, 3) capturing instant starting amps of a compressor (e.g., at a speed of 50 data/sec), 4) recording cooling amps and cooling time, 5) recording heating amps and heating time, 6) detecting increasing temperature in a heating tank or temperature decrease in a cooling tank, 7) sending any test data to the communication central module upon completion, 8) monitoring ambient temperature and relative humidity to equalize environment temperature and humidity changes in the data, 9) auto-calibrating the temperature probe 34 and current sensor of pre-tester 24, and/or 10) completing hardware diagnostics at start-up of system 10.

Pre-tester 24 can be adapted to specific testing parameters for various models of liquid dispensers 20. Pre-tester 24 can be configured to determine one or more parameters of liquid dispenser 20 including compressor instant amps, cooling amps, heating amps, cut in/off time, heating temperature, cooling temperature or a combination thereof. Pre-tester 24 can send the parameter information of liquid dispenser 20 to database management system 80 via communication central module 60.

Database management system 80 can be programmed with an algorithm to determine whether the testing data collected by pre-tester 24 is within or outside of predetermined specifications (e.g., criteria for pass/fail status). For example, database management system 80 can analyze the parameters to determine if they meet the standards for operability as pre-determined or set by a manufacturer or user for the particular liquid dispenser 20 being tested. The collected testing data can be compared to standard/predetermined values to tell if liquid dispenser 20 is functioning properly. A user can be allowed to monitor testing status, review test results and/or edit specifications per model of the liquid dispenser 20.

Figure 3:
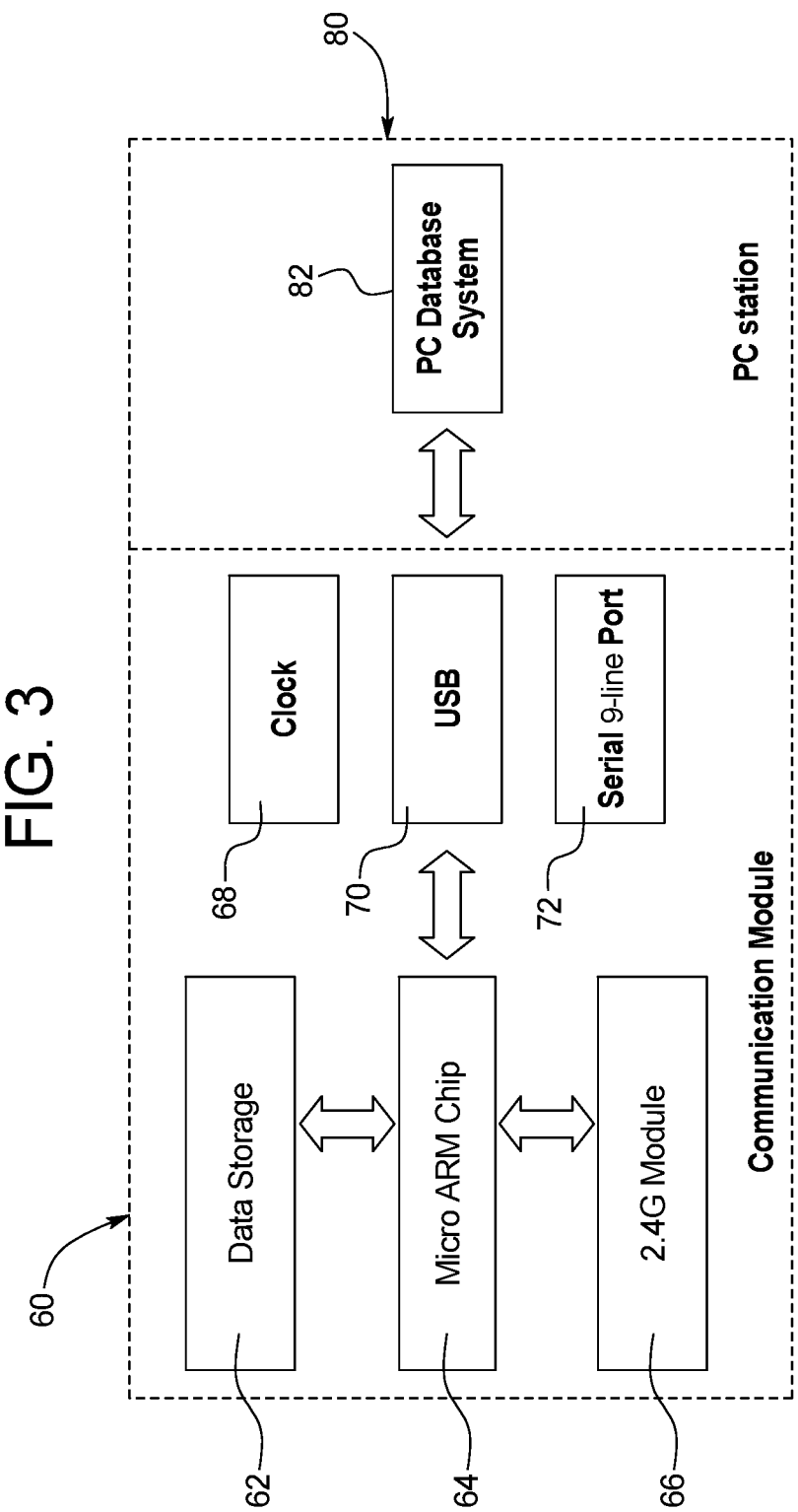
FIG. 3 shows the components of a communication central module in an embodiment of the present disclosure.

In an embodiment, communication central module 60 is configured to receive information from at least one of pre-tester 24 or testing device 40. As shown in FIG. 3, communication central module 60 can include a data storage unit 62, a microcontroller or intelligence chip (e.g., Micro ARM Chip) 64, a wireless communication module 66 that enables wireless communication (e.g., 2.4G), a clock 68, a Universal Serial Bus ("USB") port 70 and a communication port 72 that is designed for extended connection with other devices.

Wireless communication module 66 offers a few advantages. First, no cabling would be necessary. Second, less frequent plug-in/plug-out of devices would prolong the life span of testing and diagnosing system 10.

Non-limiting examples of the main functions of communication central module 60 include: 1) responding to database management system 80 commands through the USB connection, 2) sending testing parameters from database management system 80 to pre-testers 24 via a wireless connection, 3) monitoring on-line/off-line manufacturing status of pre-testers 24 and responding modules 90, 4) acquiring testing data and results from pre-testers 24 and responding modules 90, and/or 5) supporting temporary data archiving for a specified time (e.g., latest month).

In an embodiment, communication central module 60 is configured to monitor environmental temperature and humidity. For example, the environmental temperature and humidity can be monitored using an internal or external temperature sensor and humidity sensor (not shown). Communication central module 60 can relay this information to database management system 80 to be used for further analysis.

Database management system 80 is configured to operate, monitor and control one or more of pre-tester 24, testing device 40 or communication central module 60. As shown in FIGS. 1 and 3, database management system 80 can include a database system 82, a display 84, an input device 86 (e.g., keyboard) and having printing capabilities. For example, database management system 80 can print out the results of the testing and diagnoses of the heating or cooling apparatus on a label that can be applied to the apparatus for future reference. Database management system 80 can run an suitable software programs for collecting and analyzing data (e.g., Microsoft Office Access, VC++ basis). Database management system 80 can be, for example, connected to communication central module 60 using a USB connection.

Non-limiting examples of the main functions of database management system 80 include: 1) displaying working status (on-line/off-line) of pre-tester 24 and responding module 90 within a specified time period (e.g., 1 min), 2) synchronizing testing parameters and standards, 3) displaying real-time testing data for a specified time period (e.g., every 2 min) and simulating/displaying a chart/curve, and/or 4) export data to a spreadsheet (e.g., EXCEL®) database that supports data sorting. Real-time, actual testing data can be recorded in database management system 80. In the meantime, the amps/hot temperature/time curve can be plotted on display 84 as one of the user-friendly features of database management system 80.

As shown in FIG. 1, testing and diagnosing system 10 can further include a testing device 40 that is configured for evaluating one or more conditions in liquid dispenser 20 and is in communication with liquid dispenser 20. Testing device 40 can include any suitable device for evaluating one or more conditions in a heating or cooling apparatus such as, for example, an electrical safety tester (e.g., hi-pot tester) and/or an air leakage detector.

As further shown in FIG. 1, a responding module 90 is configured to relay information between testing device 40 and communication central module 60. Responding module 90 is a device that can assist in testing an electrical/air leakage, collect the relevant data from the leakage and send the data sent to database management system. If something is wrong, responding module 90 can have the relevant data printed out on a printer via database management system 80. This print-out can be used by a repair person/center to quickly identify what needs to be repaired.

Responding module 90 can adopt the same firmware design as in communication central module 60. The communication devices (e.g., COM port) of responding module 90 can accommodate any model of testing devices 40 with open protocols.

Figure 4:
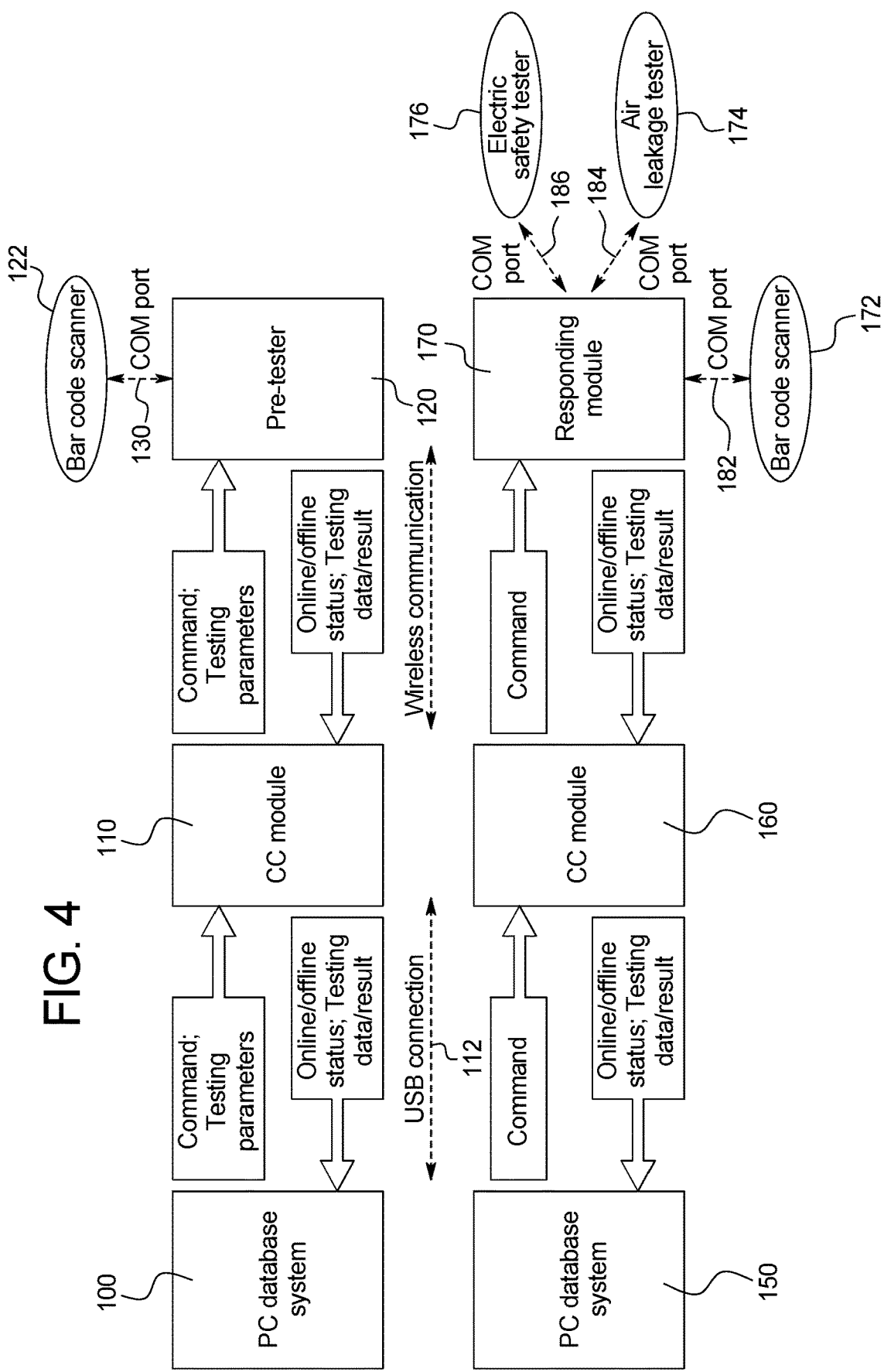
FIG. 4 shows the communication paths among the pre-tester, responding module, communication central module and database management system in an embodiment of the present disclosure.

FIG. 4 illustrates embodiments of the communication routes between a pre-tester 120 and a database management system 100 or a responding module 170 and a database management system 150. It should be appreciated that pre-tester 120 and responding module 170 can communicate with the same database management system.

Pre-tester 120 can include bar code scanner 122 in communication with pre-tester 120 using any suitable communication device 130 (e.g., COM port). Pre-tester 120 can communicate with a communication central module 110 via a wireless communication. Communication central module 110 can communicate with database management system 100 using a USB connection 112.

Responding module 170 can include bar code scanner 172, an air leakage detector 174 and an electrical safety tester 176 in communication with responding module 170 using any suitable communication devices 182, 184 and 186 (e.g., COM ports), respectively. Responding module 170 can communicate with a communication central module 160 via a wireless communication. Communication central module 160 can communicate with database management system 150 using a USB connection 112.

The following methods utilize the systems discussed herein. In a general embodiment, the present disclosure provides a method for testing and diagnosing malfunctions in a liquid dispenser during manufacturing of the liquid dispenser. The method can be performed along an assembly line for the liquid dispensers at a manufacturing plant. The method comprises testing the manufactured (e.g., newly or repaired based on a return) liquid dispenser having a water tank with at least one of an electrical safety tester or an air leakage detector to preliminarily determine if there are any electrical deficiencies or air leaks in the liquid dispenser.

The electrical safety tester can be connected to the electrical system of the liquid dispenser. The air leakage detector can be connected to any air or water lines of the liquid dispenser. Information from the electrical safety tester and/or air leakage detector can be relayed to a database management system via a responding module in communication with the electrical safety tester and/or air leakage detector. The database management system can display the results of the tests from the electrical safety tester and/or air leakage detector to an operator who can determine whether the liquid dispenser should be fixed at this step.

After the tests from the electrical safety tester and/or air leakage detector are done, the method further comprises measuring an electrical current in a circuit of the liquid dispenser and a temperature change of water in the water tank using a pre-tester configured to test for and collect testing data regarding the operational status of the liquid dispenser. A pass/fail status of the liquid dispenser is then determined based on the measured electrical current and the temperature change when compared to pre-set parameters of the electrical current and the temperature change for the liquid dispenser. It should be appreciated that each liquid dispenser can have its own pre-set parameters for the electrical current and the temperature change. The method can further comprise printing out the pass/fail status of the dispenser after the pass/fail status has been determined.

In an embodiment, a separate pre-tester can be assigned and connected to each liquid dispenser in the manufacturing line. In this regard, the pre-tester can scan a bar code located on the liquid dispenser with a bar code scanner in communication with the pre-tester to determine pre-set pass/fail parameters for the specific liquid dispenser. This also allows mass testing of the liquid dispensers (e.g., up to 200 at the same time) to be done in a short amount of time. The information from each of the pre-testers can be sent to a communication central module to be further relayed to the database management system where it can be organized and analyzed.

In another embodiment, the present disclosure provides a method for testing and diagnosing malfunctions in a liquid dispenser. For example, this method allows for testing to be done at a point-of-use location such as at a user's home or office. The method comprises connecting a pre-tester to a liquid dispenser including a water tank. The pre-tester is configured to receive data regarding the operational status of the liquid dispenser. The method further comprises measuring an electrical current in a circuit of the liquid dispenser and a temperature change of water in the water tank using the pre-tester, and determining a pass/fail status of the liquid dispenser based on the measured electrical current and the temperature change when compared to pre-set parameters of the electrical current and the temperature change for the liquid dispenser.

The pre-tester information can be sent to a database management system for analysis and display. The database management system can be, for example, in the form of laptop or other computer accessible via the internet or other wireless communication.

Prior to testing via the pre-tester, a bar code located on the liquid dispenser can be scanned with a bar code scanner in communication with the pre-tester to determine pre-set pass/fail parameters for the liquid dispenser. When the bar code of the water cooler is scanned and distributed to the pre-tester, related testing parameters and standards will be chosen specifically for the liquid dispenser. The pass/fail status of the dispenser can be printed out after the pass/fail status has been determined by the pre-tester. Further testing of the liquid dispenser can be done with at least one of an electrical safety tester or an air leakage detector.

In still another embodiment, the present disclosure provides a method for testing and diagnosing malfunctions in a heating or cooling apparatus. The method comprises testing a heating or cooling apparatus with at least one of an electrical safety tester or an air leakage detector. The heating or cooling apparatus includes a heated or cooled unit. The method further comprises measuring an electrical current in a circuit of the heating or cooling apparatus and a temperature change of the heated or cooled unit using a pre-tester configured to test for and collect testing data regarding the operational status of the heating or cooling apparatus. A pass/fail status of the heating or cooling apparatus is determined based on the measured electrical current and the temperature change when compared to pre-set parameters of the electrical current and the temperature change for the heating or cooling apparatus.

The heating or cooling apparatus can be cleaned if the heating or cooling apparatus receives a pass from the pre-tester, and testing the heating or cooling apparatus with at least one of an electrical safety tester or an air leakage detector. Alternatively, the heating or cooling apparatus can be repaired if the heating or cooling apparatus receives a fail from the pre-tester.

Improvements achieved by embodiments of the present disclosure include shortening the total testing time for liquid dispensers, automatically analyzing the data/result supplied by the pre-tester (which can ease the operation and reduce labor costs), acquiring actual testing data for function/failure analysis and production improvement, tracking faults according to different factors (e.g., production year, manufacture, model, parts/components, etc.), printing out labels with fault descriptions and possible reason for repair as a reference, accommodating varies models of liquid dispensers, integrating electric safety tester and air leakage detectors used on-line during manufacturing, and/or sending test data to database management system.

The testing and diagnosing system can be a fully automatic system to test and diagnose the malfunctions of different types of heating/cooling apparatuses. Data collection can be done via wireless connection, which minimizes equipment needs and cost. The testing and diagnosing system can be adapted to other testing equipments with standard protocols.

By examination of current and cut-off durations of the heating/cooling apparatuses to tell if they are functioning properly, this analysis can allow the testing and diagnosing system to be used for testing and diagnosing malfunctions of other home appliances. The on-line manufacturing testing and diagnosing system can also be integrated into a portable system for off-line tests, which is more convenient for maintenance service on the consumer side.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A liquid dispenser testing and diagnosing system comprising:
   a liquid dispenser configured with individual pre-set parameters for an electrical current and a temperature change;

a pre-tester configured to test for and collect testing data regarding an operational status of the liquid dispenser, the pre-tester comprising a pre-test box, a bar code scanner, and a temperature probe in communication with the pre-test box, the temperature probe configured to be inserted into the liquid dispenser for detecting the temperature change, the bar code scanner in communication with a bar code data distributor to send bar code data to the bar code data distributor, the bar code data distributor configured to distribute the bar code data to the pre-test box, the pre-test box activated upon receiving the bar code data;

the pre-tester is configured for (1) cutting off a power supply to the liquid dispenser in case of a short circuit, (2) capturing instant starting amps of a compressor, and (3) monitoring ambient temperature and relative humidity to equalize environment temperature and humidity changes in the data;

a testing device in communication with the liquid dispenser and configured for generating measurements from evaluating one or more conditions in the liquid dispenser;

a communication central module communicatively connected to the pre-tester and the testing device for the pre-tester to send the testing data to the communication central module and the testing device to send the measurements to the communication central module, the communication central module configured to receive the measurements from the testing device and the testing data from the pre-tester; and a database management system configured to operate, monitor and control at least one of the testing device, the pre-tester or the communication central module, the database management system is programmed with an algorithm to determine whether the testing data is within or outside of the pre-set parameters for the electrical current and the temperature range.

2. The liquid dispenser testing and diagnosing system of claim 1, wherein the communication central module is configured to monitor environmental temperature and humidity.

3. The liquid dispenser testing and diagnosing system of claim 1, wherein the testing device comprises an electrical safety tester.

4. The liquid dispenser testing and diagnosing system of claim 1, wherein the testing device comprises an air leakage detector.

5. The liquid dispenser testing and diagnosing system of claim 1 comprising a responding module configured to relay information between the testing device and the communication central module.

6. The liquid dispenser testing and diagnosing system of claim 1, wherein the database management system includes a computer display.

7. The liquid dispenser testing and diagnosing system of claim 1, wherein the pre-tester is further configured to determine a parameter of the liquid dispenser selected from the group consisting of compressor instant amps, cooling amps, heating amps, cut in/off time and combinations thereof.

8. The liquid dispenser testing and diagnosing system of claim 1, wherein cutting off the power supply to the liquid dispenser comprises cutting off a power supply to the heating or cooling apparatus.

9. The liquid dispenser testing and diagnosing system of claim 1, wherein the pre-tester is configured to complete hardware diagnostics upon start-up of the system.

10. A system for testing and diagnosing malfunctions in a heating or cooling apparatus, the system comprising:
a heating or cooling apparatus configured with individual pre-set parameters for an electrical current and a temperature change;
a testing device configured for generating measurements from monitoring one or more conditions in the heating or cooling apparatus;
a pre-tester configured to test for and collect testing data by measuring an electrical current and a temperature change in the heating or cooling apparatus, the pre-tester comprising a pre-test box, a bar code scanner, and a temperature probe in communication with the pre-test box, the temperature probe configured to be inserted into the heating or cooling apparatus for detecting the temperature change, the bar code scanner in communication with a bar code data distributor to send bar code data to the bar code data distributor, the bar code data distributor configured to distribute the bar code data to the pre-test box, the pre-test box activated upon receiving the bar code data;
the pre-tester is configured for (1) cutting off power supply to the liquid dispenser in case of a short circuit, (2) capturing instant starting amps of a compressor, and (3) monitoring ambient temperature and relative humidity to equalize environment temperature and humidity changes in the data;
a communication central module configured to receive the measurements from the testing device based on the monitoring by the testing device and the testing data from the pre-tester and configured to monitor environmental temperature and humidity; and
a database management system configured to operate, monitor and control at least one of the testing device, the pre-tester or the communication central module, the database management system is programmed with an algorithm to determine whether the one or more conditions are within or outside of the pre-set parameters for the electrical current and the temperature range.

11. The system of claim 10 further comprising a responding module configured to relay information between the testing device and the communication central module.

12. The system of claim 10, wherein the testing device comprises an electrical safety tester.

13. The system of claim 10, wherein the testing device comprises an air leakage detector.

14. The system of claim 10, wherein the database management system includes a computer display.

15. The system of claim 10, wherein the pre-tester is further configured to determine a parameter of the heating or cooling apparatus selected from the group consisting of compressor instant amps, cooling amps, heating amps, cut in/off time and combinations thereof.

16. The system of claim 10, wherein the pre-tester is further configured to cut off a power supply to the heating or cooling apparatus in case of a short circuit.

17. The system of claim 10, wherein the pre-tester is further configured to complete hardware diagnostics upon start-up of the system.

18. A method for testing and diagnosing malfunctions in a liquid dispenser during manufacturing of the liquid dispenser, the method comprising:
acquiring pre-set parameters for an electrical current and a temperature range of the liquid dispenser;
testing the liquid dispenser with at least one of an electrical safety tester or an air leakage detector, the liquid dispenser comprising a water tank;

measuring the electrical current in a circuit of the liquid dispenser and a temperature change of water in the water tank using a pre-tester configured to test for and collect testing data regarding the operational status of the liquid dispenser, the pre-tester comprising a pre-test box, a bar code scanner, and a temperature probe in communication with the pre-test box, the temperature probe is inserted into the water tank for detecting the temperature change, the bar code scanner in communication with a bar code data distributor to send bar code data to the bar code data distributor, the bar code data distributor distributes the bar code data to the pre-test box, the pre-test box is activated upon receiving the bar code data;

determining a pass/fail status of the liquid dispenser based on the measured electrical current and the temperature change when compared to the pre-set parameters of the electrical current and the temperature change for the liquid dispenser being tested;

cutting off power supply to the liquid dispenser in case of a short circuit using the pre- tester:

capturing instant starting amps of a compressor using the pre-tester; and monitoring ambient temperature and relative humidity to equalize environment temperature and humidity changes in the data using the pre-tester.

19. The method of claim 18 further comprising:
cleaning the liquid dispenser if the liquid dispenser receives a pass from the pre-tester; and
testing the washed liquid dispenser with at least one of the electrical safety tester or the air leakage detector.

20. The method of claim 18 further comprising printing out the pass/fail status of the dispenser after the pass/fail status has been determined, the printing is performed by a printing device provided by a database management system communicatively connected to the pre-tester.

21. The method of claim 18 further comprising scanning a bar code located on the liquid dispenser with the bar code scanner in communication with the pre-tester to determine pre-set pass/fail parameters for the liquid dispenser.

22. The method of claim 18, wherein the pre-tester is in communication with a database management system comprising a computer display.

23. The method of claim 18, wherein the pre-tester is further configured to determine a parameter of the liquid dispenser selected from the group consisting of compressor instant amps, cooling amps, heating amps, cut in/off time and combinations thereof.

24. The method of claim 18, wherein the electrical safety tester and the air leakage detector are in communication with a responding module that is in communication with a database management system.

25. A method for testing and diagnosing malfunctions in a liquid dispenser, the method comprising:
acquiring pre-set parameters for an electrical current and a temperature range of the liquid dispenser;
testing the liquid dispenser with a testing device comprising at least one of an electrical safety tester or an air leakage detector to generate measurements;
displaying the measurements from the testing device;
connecting a pre-tester to the liquid dispenser, the liquid dispenser comprising a water tank, the pre-tester configured to test for and collect testing data regarding the operational status of the liquid dispenser, the pre-tester comprising a pre-test box, a bar code scanner, and a temperature probe in communication with the pre-test box, the temperature probe is inserted into the water tank for detecting the temperature change, the bar code scanner in communication with a bar code data distributor to send bar code data to the bar code data distributor, the bar code data distributor distributes the bar code data to the pre-test box, the pre-test box activated upon receiving the bar code data;

measuring an electrical current in a circuit of the liquid dispenser using the pre-tester;

determining a pass/fail status of the liquid dispenser based on the measured electrical current and the temperature change when compared to the pre-set parameters of the electrical current and the temperature change for the liquid dispenser being tested;

cutting off power supply to the liquid dispenser in case of a short circuit using the pre-tester;

capturing instant starting amps of a compressor using the pre-tester; and monitoring ambient temperature and relative humidity to equalize environment temperature and humidity changes in the data using the pre-tester.

26. The method of claim 25 further comprising scanning a bar code located on the liquid dispenser with the bar code scanner to determine pre-set pass/fail parameters for the scanned liquid dispenser.

27. The method of claim 25, wherein the pre-tester is in communication with a database management system comprising a computer display.

28. The method of claim 25 further comprising printing out the pass/fail status of the dispenser after the pass/fail status has been determined by the pre- tester.

29. The method of claim 25, wherein the pre-tester is further configured to determine a parameter of the liquid dispenser selected from the group consisting of compressor instant amps, cooling amps, heating amps, cut in/off time and combinations thereof.

30. A method for testing and diagnosing malfunctions in a heating or cooling apparatus, the method comprising:
acquiring pre-set parameters for an electrical current and a temperature range of the liquid dispenser;
testing a heating or cooling apparatus with at least one of an electrical safety tester or an air leakage detector, the heating or cooling apparatus comprising a heated or cooled unit;
measuring the electrical current in a circuit of the heating or cooling apparatus and the temperature change of the heated or cooled unit using a pre-tester configured to measure the electrical current and the temperature change in the heating or cooling apparatus, the pre-tester comprising a pre-test box, a bar code scanner, and a temperature probe in communication with the pre-test box, the temperature probe is inserted into the heating or cooled apparatus for detecting the temperature change, the bar code scanner in communication with a bar code data distributor to send bar code data to the bar code data distributor, the bar code data distributor distributes the bar code data to the pre-test box, the pre-test box activated upon receiving the bar code data;
determining a pass/fail status of the heating or cooling apparatus based on the measured electrical current and the temperature change when compared to the pre-set parameters of the electrical current and the temperature change for the heating or cooling apparatus being tested;
cutting off power supply to the liquid dispenser in case of a short circuit using the pre-tester;
capturing instant starting amps of a compressor using the pre-tester; and monitoring ambient temperature and relative humidity to equalize environment temperature and humidity changes in the data using the pre-tester.

31. The method of claim 30 further comprising scanning the heating or cooling apparatus using the bar code scanner to determine the pre-set parameters of the electrical current and the temperature change for the heating or cooling apparatus.

32. The method of claim 30 further comprising wirelessly printing a label for the heating or cooling apparatus based on the pass/fail status, the printing is performed by a printing device provided by a database management system communicatively connected to a wireless communication module communicatively connected to the pre-tester.

* * * * *